United States Patent [19]

Egan, Jr.

[11] 4,051,853
[45] Oct. 4, 1977

[54] DIAPER WITH EXTENSIBLE FASTENER

[75] Inventor: Francis L. Egan, Jr., Arlington Heights, Ill.

[73] Assignee: Colgate-Palmolive Company, New York, N.Y.

[21] Appl. No.: 712,612

[22] Filed: Aug. 9, 1976

[51] Int. Cl.² .............................................. A61F 13/16
[52] U.S. Cl. .................................. 128/287; 128/284; 24/DIG. 11
[58] Field of Search ................... 128/284, 287, 290 R, 128/290 H; 24/73 VA, DIG. 11

[56] References Cited
U.S. PATENT DOCUMENTS

| 3,245,407 | 4/1966 | Mason | 128/284 |
| 3,620,217 | 11/1971 | Gellert | 128/284 |
| 3,707,969 | 1/1973 | Sanford | 128/287 |
| 3,750,669 | 8/1973 | De Luca | 128/287 |
| 3,800,796 | 4/1974 | Jacob | 128/284 |
| 3,853,129 | 12/1974 | Kozak | 128/287 |

Primary Examiner—Aldrich F. Medbery
Attorney, Agent, or Firm—Powell L. Sprunger

[57] ABSTRACT

A disposable diaper comprising, an absorbent pad assembly, and a tape fastener comprising an elongated pressure-sensitive tape strip having a first section attached to a surface of the pad assembly and a second securement section extending from the first section in a longitudinal direction of the tape strip for securing the diaper about an infant. The tape strip has a backing of a non-reinforced, extensible polymeric film, with the film having an ultimate elongation of greater than 50% in the longitudinal direction of the tape strip, and having modulus properties such that the film has an elongation of 50% at 5–10 lbs./in. width of force as applied to the second section of the tape strip in the longitudinal direction thereof.

7 Claims, 8 Drawing Figures

DIAPER WITH EXTENSIBLE FASTENER

BACKGROUND OF THE INVENTION

The present invention relates to absorbent articles, and more particularly to disposable diapers.

A various assortment of disposable diapers have been proposed for use on infants, and have become increasingly popular since they may be discarded after a single use and need not be laundered. Such diapers are normally constructed having a fluid impervious backing sheet, a fluid pervious cover or top sheet, and an absorbent pad between the backing and cover sheets. Many of the current disposable diapers have also been provided with tape fasteners which are usually in the form of a pressure-sentitive tape strip having a first end section secured to the backing or cover sheets, normally the former, and a second end section which is used to secure the diaper about the infant.

Of course, a critical factor in the suitability of the diapers is the cost to the consumer, since the diapers are not reused, and relatively thin materials have been proposed for the diaper backing and cover sheets in order to reduce the cost of the required manufacturing materials. However, it has been found that considerable forces are applied to the tape strips during placement and use of the diaper, and, in many instances, the applied forces are sufficiently large to cause rupture of the thin backing or cover sheets at the point where the tape strips are secured to the diaper. Thus, the tape strips are frequently torn from the diapers, resulting in a relatively useless diaper without a suitable tape fastener.

In the past, all of the tape strip backings, such as paper, cloth, spun bonded polyolefin, or reinforced polyethylene, sold on diapers known to the applicant have been relatively inextensible, e.g., the backings have an ultimate elongation of approximately 3-6%, or have otherwise required relatively large forces to obtain extensibility. In either event, it has been discovered that the relative inextensibility of the tape strips contributes significantly to the incidence of tape strip rupture or shear from the diaper. On the other hand, a tape backing which is too extensible, such as rubber, exhibits excess stretch during attachment to the diaper which makes placement of the fastener difficult, may result in a loose fitment of the diaper about the infant, and such a fastener may require different components which increases the cost of manufacture.

SUMMARY OF THE INVENTION

A principal feature of the present invention is the provision of a disposable diaper having an improved tape fastener.

The diaper of the present invention comprises, an absorbent pad assembly, and a tape fastener comprising a pressure-sensitive tape strip having a first section attached to a surface of the pad assembly and a second securement section extending from the first section in a longitudinal direction of the tape strip for securing the diaper about an infant. The tape strip has a backing of a non-reinforced, extensible, polymeric film, with the film having an ultimate elongation of greater than 50% in the longitudinal direction of the tape strip, and having modulus properties such that the film has an elongation of 50% at 5-10 lbs./in. width of force as applied to the second section of the tape strip in a longitudinal direction thereof.

A feature of the present invention is that the extensible backing reduces the effective forces applied to the pad assembly through the tape strip.

Thus, another feature of the invention is that the extensible backing minimizes the possibility of tape strip rupture from the pad assembly during placement and use of the diaper.

Yet another feature of the invention is that the film backing prevents over-extension of the tape strip which otherwise may result in a loose fitment of the diaper about the infant.

Still another feature of the invention is that the strip backing may be made of one-piece construction at a reduced cost.

Further features will become more fully apparent in the following description of the embodiments of this invention and from the appended claims.

DESCRIPTION OF THE PREFERRED EMBODIMENTS

Figure 1:
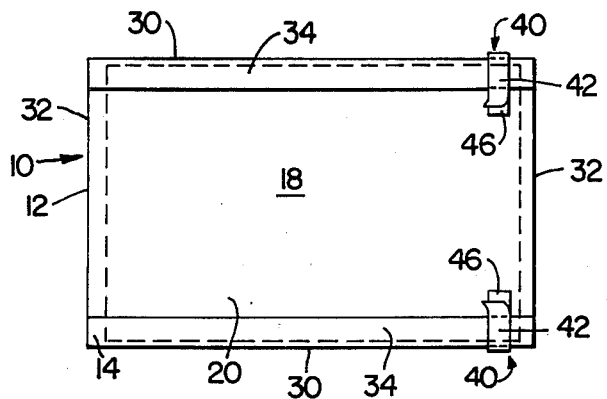
FIG. 1 is a front plan view of a disposable diaper having a tape fastener according to the present invention.

Referring now to FIGS. 1-4, there is shown a disposable diaper generally designated 10 having an absorbent pad assembly 12. The pad assembly 12 has a fluid impervious backing sheet 14, such as polyethylene, defining a back surface 16 of the pad assembly 12, a fluid pervious top or cover sheet 18, such as a nonwoven material, defining a substantial portion of a front surface 20 of the pad assembly 12, and an absorbent pad 22 intermediate the backing sheet 14 and cover sheet 18. As shown, the pad 22 may have front and back wadding sheets 24 and 26, respectively, covering opposed surfaces of a pad portion 28, such as a comminuted wood pulp termed in the art as fluff, in order that the front and back wadding sheets 24 and 26 maintain the structural integrity of the pad portion 28. The pad assembly 12 has a pair of side edges 30, and a pair of end edges 32 connecting the side edges 30. As shown, the backing sheet 14 may have lateral side margins 34 folded over and secured to the cover sheet 18, such that the backing sheet margins 34 cover laterial side margins of the absorbent pad 22.

Figure 2:
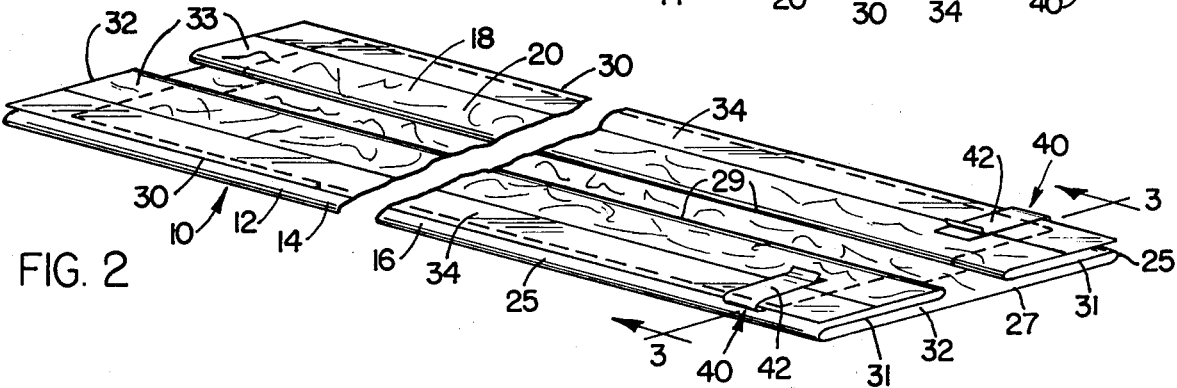
FIG. 2 is a fragmentary perspective view showing the diaper of FIG. 1 as folded into a box-pleat configuration.
Figure 3:
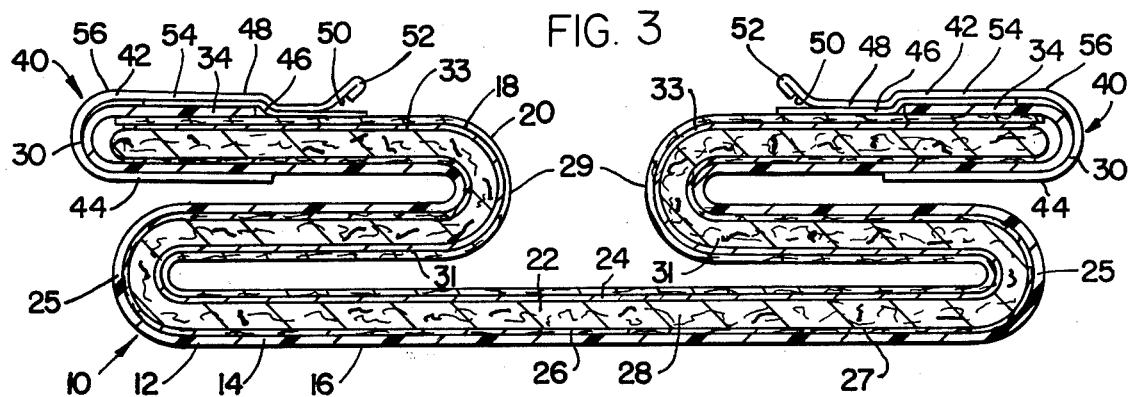
FIG. 3 is a sectional view taken substantially as indicated along the line 3—3 of FIG. 2.
Figure 4:
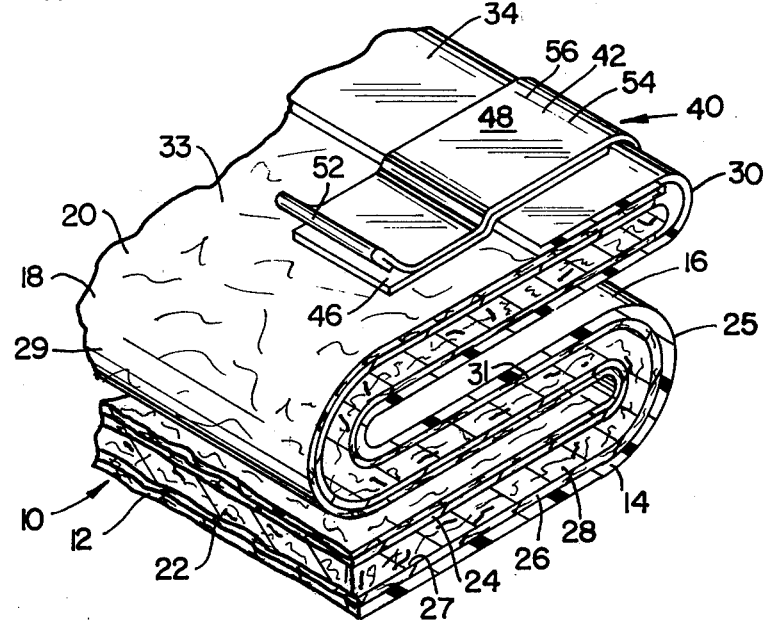
FIG. 4 is a fragmentary perspective view, taken partly in section and on an enlarged scale, of the diaper of FIG. 2.

With reference to FIGS. 2-4, the pad assembly 12 may be folded into a box-pleat configuration in the following manner. The pad assembly 12 is folded along a pair of first longitudinal fold lines 25 defining a longitudinally extending central panel 27, and along a pair of second longitudinal fold lines 29 defining a pair of first panels 31 extending between the fold lines 25 and 29 and overlying the central panel 27, and defining a pair of outermost panels 33 extending from the fold lines 29 and overlying the first panels 31.

As shown in FIGS. 1-4, and 8, the diaper 10 also has a pair of tape fasteners 40 adjacent the side edges 30 of the pad assembly 12 which are used to secure the diaper about an infant during displacement of the diaper. Each of the tape fasteners 40 has an elongated pressure-sensitive tape strip 42 having a backing 54 defining an outer surface 56 of the tape strip, adhesive 50 on an inner surface 58 of the backing 54, and a first end section 44 secured by the adhesive 50 to the backing sheet 14 adjacent the side edge 30 of the pad assembly 12. Each of the tape fasteners 40 also has a release sheet 46 secured to the front surface 20 of the pad assembly 12 adjacent the side edge 30, and each of the tape strips 42 has a second securement end section 48 folded over the front surface of the pad assembly and being releasably attached by the adhesive 50 to an outer release surface of the release sheet 46. The tape strips 42 may also have folded over outer ends 52 defining tabs to facilitate removal of the securement sections 48 of the tape strips 42 from the release sheets 46. In use, the ends or tabs 52 of the tape strips 42 are used to peel the securement sections 48 of the tape strips 42 from the release sheets, after which the securement sections 48 are attached to remote portions of the diaper in order to fasten the diaper about an infant.

In accordance with the present invention, the backings 54 of the tape strips 42 are made from a non-reinforced, extensible, polymeric film, such as a low density polyethylene film. The film has an ultimate elongation of greater than 50%, and preferably an ultimate elongation of 300-750%, in the longitudinal direction of the tape strip 42 as measured in the direction extending between the first and second strip sections 44 and 48. The backing has modulus properties such that the film has an elongation of 50% at 5-10 lbs./in. width of force as applied to the second securement sections 48 of the tape strips 42 in the longitudinal direction along the tape strips. The backing film has a breaking strength in the longitudinal direction of 7-12 lbs./in. width of force, and preferably has a thickness of from 4-10 mils.

Figure 7:
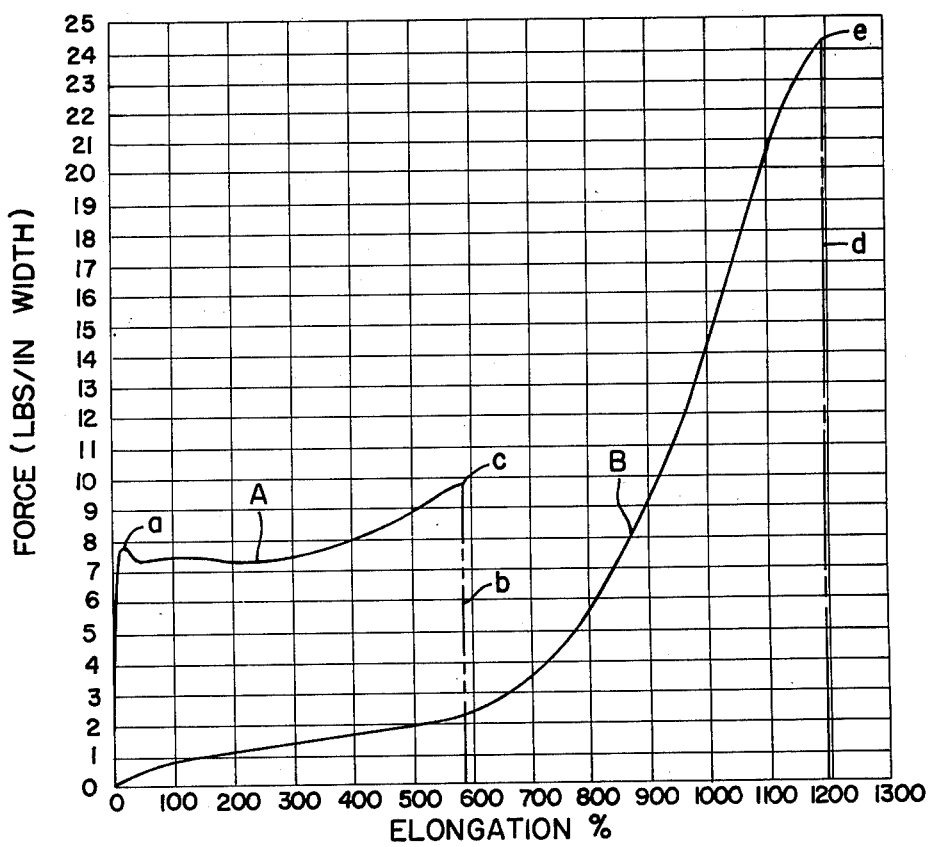
FIG. 7 is a chart illustrating modulus properties of materials.

With reference to FIG. 7, a chart of modulus properties is set forth for materials showing elongation (in percentage) of the materials as plotted against the amount of force (in lbs/in. width) of the materials as applied in the longitudinal direction of the materials. The plot designated A illustrates the modulus properties of a polymeric film according to the present invention, in this case a preferred material of low density polyethylene having a thickness of approximately 7.25 mils. The plot B illustrates the modulus properties of an even thicker sheet of typical rubber having a thickness of approximately 9 mils. As shown, the polymeric film shown in plot A has a yield point ($a$) of approximately 7.9 lbs/in. width, an ultimate elongation ($b$) of approximately 585%, and a breaking strength ($c$) of approximately 9.8 lbs/in. width. The polymeric film backing reaches its yield point ($a$) at a relatively slight elongation of approximately 15% responsive to application of forces in the longitudinal direction of the tape strip, after which relatively constant forces of approximately 7 to 8 lbs/in. width cause extension of the film until it reaches approximately 400% elongation, after which the forces required to extend the film gradually increase until the breaking strength ($c$) is reached at approximately 585% elongation of the film.

In contrast, the rubber sheet illustrated in plot B, due to its increased elasticity, achieves an elongation of 585% with the relatively slight force of 2.25 lbs/in. width. As shown, the forces required to extend the rubber sheet gradually increase until an ultimate elongation ($d$) of approximately 1190% is obtained at a breaking strength ($e$) of approximately 24 lbs/in. width. The relative forces required to achieve varying elongations of the polymeric film and rubber sheet are summarized in the table below:

|  | Force (lbs/in. width) to Elongate | | | | | |
|---|---|---|---|---|---|---|
|  | 5% | 15% | 25% | 50% | 100% | 500% |
| Polymeric Film | 5.2 | 7.9 | 7.6 | 7.5 | 7.6 | 9.1 |
| Rubber Sheet | 0.05 | 0.15 | 0.2 | 0.3 | 0.4 | 2.0 |

As indicated above, it is necessary that the strip backing has an elongation of 50% at 5-10 lbs/in. width in the longitudinal direction of the strip in order to obtain the desired amount of extensibility during placement and use of the diaper. It will be seen from the table and chart of FIG. 7 that 50% elongation in the polymeric film is obtained responsive to application of approximately 7.5 lbs/in. width of force in the longitudinal direction, while a relatively insignificant force of 0.3 lbs/in. width causes 50% elongation of the rubber sheet. On the one hand, the polymeric backing film of the present invention extends in the longitudinal direction when forces of sufficient magnitude to rupture the backing sheet are applied to the tape strip, and thus minimizes the magnitude of such rupturing forces as applied in shear to the diaper in order to prevent rupture of the backing sheet. On the other hand, in contrast to the rubber sheet, the polymeric backing of the present invention prevents overextension of the tape strip responsive to smaller normal forces applied to the tape strip, thus preventing possible loose fitment of the diaper about the infant. As indicated above, in a preferred form the polymeric film achieves an elongation of 50% at 5-10 lbs/in. width of force as applied to the second section of the tape strip in a longitudinal direction, has an ultimate elongation of 300-750% in the longitudinal direction, a breaking strength of 7-12 lbs/in. width in the longitudinal direction, and may comprise a non-reinforced low density polyethylene having a thickness of from 4-10 mils.

Figure 5:
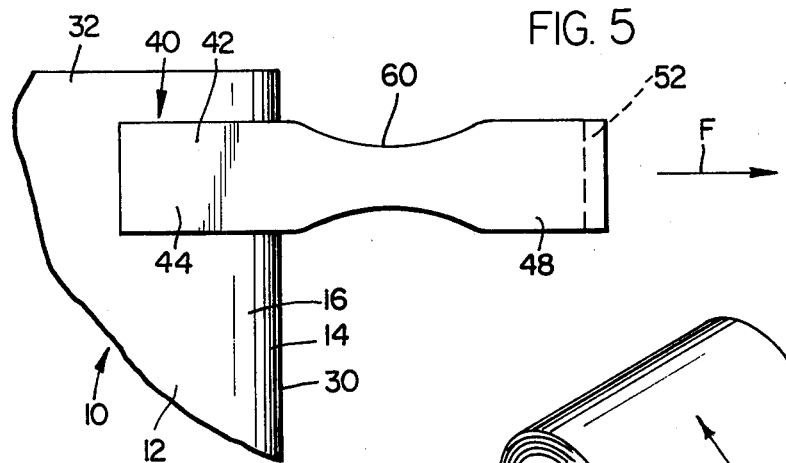
FIG. 5 is a fragmentary back plan view of the diaper of FIG. 1 illustrating extensibility of a tape strip on the tape fastener.

With reference to FIG. 5, when forces F of rupture magnitude are applied to the securement section 46 of the tape strip 42 during placement or use of the diaper, the securement section 48 extends in the longitudinal direction and necks in as at 60, such that the polymeric strip backing acts as a shock absorber to reduce forces applied in shear to the backing sheet. In this manner, the tape strip of the present invention minimizes the possibility of rupture from the pad assembly while preventing overextension of the tape strip responsive to small stresses. In contrast, the backings in the prior tape strips have either been relatively inextensible, or have only achieved elongation responsive to application of forces larger than rupturing magnitude, and, in either event, have been found a contributing factor in rupture of the tape strips from the pad assembly during placement or use of the diaper.

Figure 6:
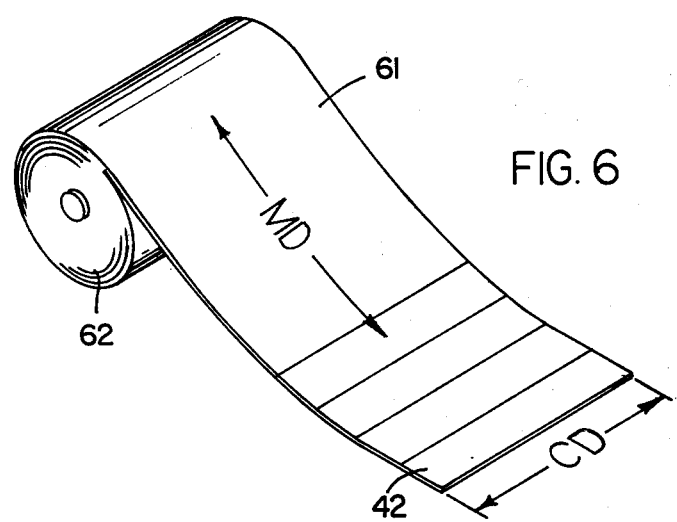
FIG. 6 is a perspective view of a tape roll.
Figure 8:
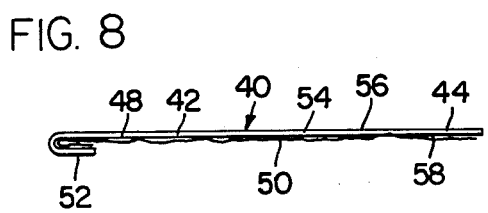
FIG. 8 is an elevational view of the tape strip.

In certain of the polymeric materials, such as polyethylene made by a calendering process, the films have different modulus characteristics in the machine direction and the cross direction transverse to the machine direction, and have the desired modulus characteristics only in the cross direction. In such cases, with reference to FIG. 6, the tape 61 is normally wound into rolls 62 with the machine direction (M.D.) of the tape backing being aligned in the longitudinal direction of the tape 61. As the outer end of the tape 61 is unwound from the roll 62 during manufacture of the diapers, the tape 61 is transversely cut to define the elongated tape strips 42 with the longitudinal direction of the tape strips 42 being aligned with the cross or transverse direction (C.D.) of the tape 61. In this manner, the desirable modulus characteristics in the longitudinal direction of the tape strips 42 are obtained by orienting the longitudinal direction of the strips 42 with the cross or transverse direction (C.D.) of the tape 61 during manufacture.

The foregoing detailed description is given for clearness of understanding only, and no unnecessary limitations should be understood therefrom, as modifications will be obvious to those skilled in the art.

I claim:

1. A disposable diaper comprising, an absorbent pad assembly, and a tape fastener comprising an elongated pressure-sensitive tape strip having a first section attached to a surface defined by a sheet of the pad assembly and a second securement section extending from the first section in a longitudinal direction of the tape strip for securing the diaper about an infant, said tape strip having means for extending and elongating in length previous to failure of said sheet when forces are applied in a longitudinal direction of the strip comprising an adhesively coated backing of a non-reinforced, extensible, polymeric film, with said film having an ultimate elongation of greater than 50% in the longitudinal direction of the tape strip, and having modulus properties such that said film has an elongation of 50% at 5-10 lbs/in. width of force as applied to the second section of the tape strip in the longitudinal direction thereof.

2. The diaper of claim 1 wherein said film has an ultimate elongation of 300-750% in the longitudinal direction.

3. The diaper of claim 1 wherein said film has a thickness of from 4-10 mils.

4. The diaper of claim 1 wherein said film comprises a low density polyethylene.

5. The diaper of claim 1 wherein said film has a breaking strength of 7-12 lbs/in. width of force in the longitudinal direction thereof.

6. The diaper of claim 1 wherein the machine direction of the film is orientated transverse to the longitudinal direction of the tape strip.

7. The diaper of claim 1 wherein said pad assembly includes a backing sheet of fluid impervious material, and in which said first section is attached to the backing sheet adjacent a side edge of the pad assembly.

* * * * *